(12) United States Patent
Uemura et al.

(10) Patent No.: US 6,252,110 B1
(45) Date of Patent: *Jun. 26, 2001

(54) METHODS FOR RECOVERING ACRYLIC ACID

(75) Inventors: Masahiro Uemura; Takahiro Takeda; Masatoshi Ueoka, all of Himeji (JP)

(73) Assignee: Nippon Shokubai Co LTD, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/104,358

(22) Filed: Jun. 25, 1998

(30) Foreign Application Priority Data

Jun. 25, 1997 (JP) ................................................. 9-168218

(51) Int. Cl.⁷ .................................................... C07C 57/02
(52) U.S. Cl. ........................... 562/598; 562/600; 203/39; 203/75; 203/DIG. 21
(58) Field of Search ..................................... 562/600, 598; 203/39, 75, DIG. 21

(56) References Cited

U.S. PATENT DOCUMENTS 4,317,926  3/1982  Sato et al. .............................. 562/532

FOREIGN PATENT DOCUMENTS

| 1151501 | 7/1963 | (DE) | ............................... | C07C/12/21 |
| 1207089 | 9/1970 | (GB) | ............................... | C07C/69/54 |
| 1211443 | 11/1970 | (GB) | ............................... | C07C/57/04 |
| 4519281 | 2/1970 | (JP) . | | |
| 5191208 | 8/1976 | (JP) | ............................... | C07C/51/50 |
| 61-36501 | 8/1986 | (JP) | ............................... | C07C/57/07 |
| 6135977 | 8/1986 | (JP) | ............................... | C07C/57/07 |

*Primary Examiner*—Paul F. Shaver

(57) ABSTRACT

A method for recovering acrylic acid from high boiling impurities containing acrylic acid dimer, acrylic acid and maleic acid at high efficiency with stability which includes the steps of (1) introducing said high boiling impurities containing acrylic acid dimer, acrylic acid and maleic acid into an acrylic acid recovery column, distilling acrylic acid from the column top and recovering the same, (2) introducing bottom liquid A from said acrylic acid recovery column into a pyrolyzing tank to decompose the acrylic acid dimer in the bottom liquid A, and (3) recirculating at least a part of bottom liquid B from said pyrolyzing tank into the acrylic acid recovery column.

10 Claims, 1 Drawing Sheet

METHODS FOR RECOVERING ACRYLIC ACID

Figure 1:
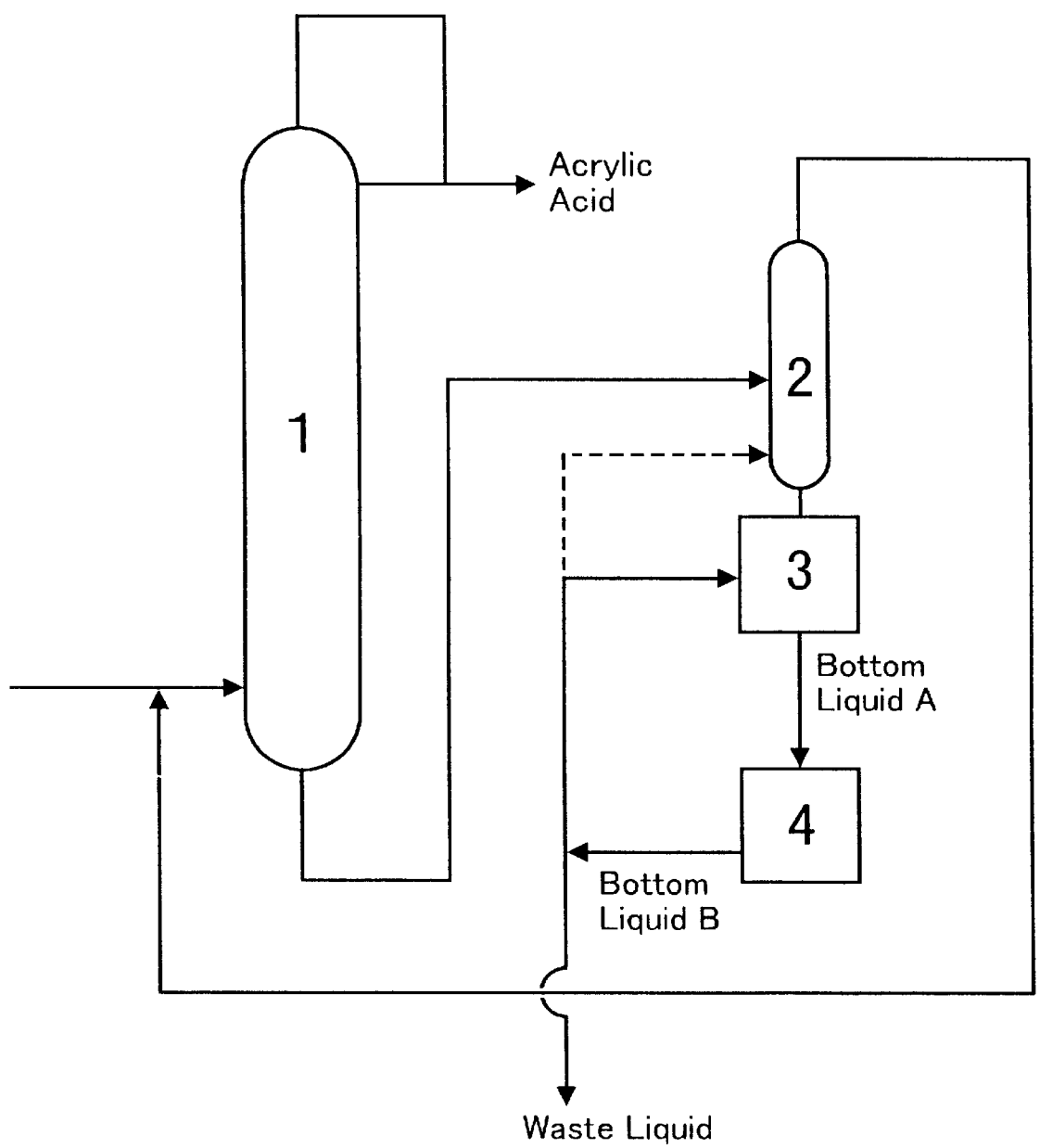

This invention relates to methods for recovering acrylic acid. More particularly, the invention relates to methods for recovering acrylic acid from high boiling impurities containing acrylic acid dimer, acrylic acid and maleic acid. Still more particularly, the invention relates to methods for efficiently and stably recovering acrylic acid from high boiling impurities containing acrylic acid dimer, acrylic acid and maleic acid, which are obtained as bottom liquid of high boiling impurities separation column in a process for producing high purity acrylic acid comprising contacting an acrylic acid-containing gas resulting from gas-phase catalytic oxidation of propylene and/or acrolein with water to trap the acrylic acid as an aqueous acrylic acid solution, distilling said aqueous solution in the presence of an azeotropic solvent to recover crude acrylic acid, and purifying the so obtained crude acrylic acid with a high boiling impurities separation column.

Conventionally, production of high purity acrylic acid through gas-phase catalytic oxidation of propylene and/or acrolein has been practiced by a method comprising contacting an acrylic acid-containing gas from the oxidation step with water to collect acrylic acid in the form of an aqueous acrylic acid solution (collection step); extracting acrylic acid from the aqueous acrylic acid solution using an appropriate extraction solvent (extraction step); separating the solvent from the resulting extract to recover crude acrylic acid (solvent separation step); and thereafter separating from the crude acrylic acid such high boiling impurities contained therein as acrylic acid dimer, maleic acid and the like, to obtain high purity acrylic acid (purification step).

Thus separated high boiling impurities contain, however, besides acrylic acid, acrylic acid dimer and therefore it is uneconomical to discard them as waste liquid as a whole.

Hence, methods have been proposed by JP Sho 45-19281 B2, JP Sho 51-91208A, JP Sho 61-35977 B2 and JP Sho 61-36501 B2, etc., to increase recovery ratio of acrylic acid by pyrolyzing the acrylic acid dimer in said high boiling impurities into acrylic acid and recovering the same.

Recently, however, instead of the above-described solvent extraction method which uses an extraction solvent for recovering acrylic acid from aqueous acrylic acid solution, azeotropic separation method using azeotropic solvents, i.e., distilling an aqueous acrylic acid solution in the presence of an azeotropic solvent which forms an azeotrope with water to cause distillation of an azeotrope of water with the solvent from the top of an azeotropic separation column and recovering acrylic acid from the bottom part of the same column, is becoming the mainstream practice.

Thus, the production method of high purity acrylic acid in the recent years normally consists of an oxidation step for producing acrylic acid through gas-phase catalytic oxidation of propylene and/or acrolein; a collection step of contacting the acrylic acid-containing gas with water and collecting the acrylic acid in the form of an aqueous acrylic acid solution; an azeotropic separation step of distilling the aqueous acrylic acid solution in an azeotropic separation column in the presence of an azeotropic solvent and recovering crude acrylic acid from bottom part of said column; and a purification step of purifying the crude acrylic acid. This purification step is normally conducted using a high boiling impurities separation column for removing high boiling impurities in the crude acrylic acid and optionally an acetic acid separation column for further removing acetic acid.

However, in such acrylic acid production process using the azeotropic separation method as described above, still the high boiling impurities separated in the purification step contain, besides acrylic acid, acrylic acid dimer, maleic acid and the like.

It is therefore desirable to recover acrylic acid from said high boiling impurities also in the high purity acrylic acid production process using the azeotropic separation method. As the recovery means, application of those methods as described in the earlier listed JP publications, which have been proposed in respect of the high purity acrylic acid production process following the solvent extraction method, may be considered.

However, when for example the apparatus for destructive distillation of acrylic acid dimer as described in JP Sho 61-36501 B2 (the first step) is used to simultaneously conduct decomposition of acrylic acid dimer and distillation of the acrylic acid formed upon said decomposition as well as that which is initially contained in the high boiling impurities, it has been found that such a problem as that the impurities mix into the product acrylic acid to reduce purity of the product is encountered.

We have discovered that the problem has its cause in the maleic acid contained in the high boiling impurities. Maleic acid is substantially completely separated and removed in the solvent extraction step in the processes using solvent extraction method and therefore does not remain in the resulting crude acrylic acid, but in processes using azeotropic separation method, it does remain in the crude acrylic acid and is mixed into the high boiling impurities separated in purification of this crude acrylic acid in a proportion of a few percent.

Such maleic acid is distilled off with acrylic acid from aforesaid apparatus for destructive distillation of acrylic acid dimer. When the distillate is recirculated to an earlier step, eg., to a high boiling impurities separation column in the purification step, with the view to recover acrylic acid therefrom, maleic acid is entrained by the distillate and condensed at the bottom of the high boiling impurities separation column to eventually mix into the product acrylic acid to reduce the latter's purity.

Maleic acid also changes into fumaric acid in the step of recovering acrylic acid from the high boiling impurities containing acrylic acid dimer, acrylic acid and maleic acid, said fumaric acid precipitates in said recovery step to interfere with stable operation.

Accordingly, therefore, the object of the present invention is to solve the above problem, that is, to provide a method for efficiently and stably recover acrylic acid from high boiling impurities containing acrylic acid dimer, acrylic acid and maleic acid, in particular, the high boiling impurities containing acrylic acid dimer, acrylic acid and maleic acid as obtained as bottom liquid of high boiling impurities separation column in a process for producing acrylic acid using azeotropic separation method.

We have discovered that the above object can be accomplished by the use of an acrylic acid recovery apparatus and an acrylic acid dimer decomposition apparatus, in place of aforesaid apparatus for destructive distillation (the first step) of acrylic acid dimer. More specifically, we have discovered that acrylic acid can be efficiently recovered from high boiling impurities without reduction in purity of product acrylic acid, by introducing said high boiling impurities into an acrylic acid recovery column (which preferably is a distillation column equipped with a thin film vaporizer), in which separating maleic acid and taking it out from the bottom of the column and recovering acrylic acid of markedly reduced maleic acid content from the column top; introducing the bottom liquid containing acrylic acid dimer, acrylic acid and maleic acid into a pyrolyzing tank, where at pyrolyzing the acrylic acid dimer; and then recirculating a part of the decomposition product into said acrylic acid recovery column.

Thus, according to the present invention, a method for recovering acrylic acid is provided, which is characterized by comprising, in recovering acrylic acid from high boiling impurities containing acrylic acid dimer, acrylic acid and maleic acid, (1) introducing said high boiling impurities containing acrylic acid dimer, acrylic acid and maleic acid, into an acrylic acid recovery column and recovering acrylic acid as it is distilled off from the top of the column, (2) introducing bottom liquid A from said acrylic acid recovery column into a pyrolyzing tank to decompose the acrylic acid dimer in the bottom liquid A, and then, (3) recirculating at least a part of bottom liquid B from said pyrolyzing tank into the acrylic acid recovery column (when the acrylic acid recovery column consists of a thin film vaporizer and a distillation column, into either one of them or both).

According to the present invention, furthermore, a method for recovering acrylic acid is provided, as an improvement of an acrylic acid recovery method comprising contacting an acrylic acid-containing gas obtained through gas-phase catalytic oxidation of propylene and/or acrolein with water to trap the acrylic acid in the form of its aqueous solution, distilling said aqueous acrylic acid solution in an azeotropic separation column in the presence of an azeotropic solvent, and purifying the crude acrylic acid obtained from the bottom part of said azeotropic separation column in a high boiling impurities separation column, said improvement comprising recovering acrylic acid from the bottom liquid of said high boiling impurities separation column (i.e., the high boiling impurities containing acrylic acid dimer, acrylic acid and maleic acid), characterized by (1) introducing said high boiling impurities containing acrylic acid dimer, acrylic acid and maleic acid into an acrylic acid recovery column composed of a distillation column equipped with a thin film vaporizer, wherein conducting distillation under conditions of 10 to 100 mmHg and at the bottom temperature of the column of 60 to 120° C., distilling acrylic acid off from the column top and recovering the same;

(2) introducing bottom liquid A from said thin film vaporizer into a pyrolyzing tank, whereat decomposing acrylic acid dimer in said bottom liquid A at temperatures of 120 to 220° C.; and thereafter (3) recirculating at least a part of bottom liquid B of said pyrolyzing tank into said thin film vaporizer and/or the distillation column, at a ratio of 1 to 20 times the high boiling impurities containing acrylic acid dimer, acrylic acid and maleic acid.

The high boiling impurities containing acrylic acid dimer, acrylic acid and maleic acid as herein referred to signify a mixture containing at least 20 weight percent of acrylic acid dimer, at least 20 weight percent of acrylic acid and 3 to 10 weight percent of maleic acid. The mixture may further contain other high boiling substances such as acrylic acid trimer. The method of this invention is used with particular convenience for recovering acrylic acid from high boiling impurities containing, besides acrylic acid dimer and acrylic acid, 5 to 10 weight % of maleic acid.

A typical example of such high boiling impurities containing acrylic acid dimer, acrylic acid and maleic acid is a bottom liquid obtained in the occasion of practicing the process comprising contacting an acrylic acid-containing gas resulting from gas-phase catalytic oxidation of propylene and/or acrolein with water to trap the acrylic acid in the form of an aqueous acrylic acid solution, distilling the aqueous solution in the presence of an azeotropic solvent, if necessary purifying the resultant crude acrylic acid with another distillation column and thereafter introducing the acrylic acid into a high boiling impurities separation column. The bottom liquid is obtained from the high boiling impurities separation column. While specific composition of the liquid cannot be generally defined as it differs depending on operation conditions selected for each of the processing steps, for example, the bottom liquid can consist of 20 to 65 weight % of acrylic acid, 30 to 60 weight % of acrylic acid dimer, 5 to 15 weight % of polymerization inhibitor (eg., hydroquinone), 3 to 10 weight % of maleic acid, and other high boiling substances.

The method of the present invention basically comprises the following steps: (1) a step of introducing high boiling impurities containing acrylic acid dimer, acrylic acid and maleic acid, which are withdrawn from the high boiling impurities separation column, into an acrylic acid recovery column (distillation column), wherein distilling the acrylic acid contained in the high boiling impurities off from the column top and recovering the same; (2) a step of withdrawing a bottom liquid A from the bottom part of said acrylic acid recovery column (thin film vaporizer), said bottom liquid A containing acrylic acid dimer, acrylic acid and maleic acid, introducing said bottom liquid A into a pyrolyzing tank to decompose the acrylic acid dimer and form acrylic acid; and (3) a step of recirculating at least a part of the bottom liquid B from the pyrolyzing tank into said acrylic acid recovery column (distillation column and/or thin film vaporizer), whereby recovering from the column top the acrylic acid which has been obtained through the pyrolysis of acrylic acid dimer contained in said bottom liquid B.

The acrylic acid recovery column to be used in the present invention is subject to no particular limitation so long as it is capable of distilling high boiling impurities containing acrylic acid dimer, acrylic acid and maleic acid. Whereas, because the high boiling impurities obtained as a bottom liquid of a high boiling impurities separation column in the above-described acrylic acid production process has high viscosity, use of a distillation column equipped with a thin film vaporizer as the acrylic acid recovery column is preferred for treating such high boiling impurities.

Hereinafter the present invention is explained in more detail, referring to an embodiment wherein a bottom liquid from a high boiling impurities separation column, which is used for purification purpose in the process for recovering acrylic acid by means of azeotropic distillation of gas-phase catalytic oxidation product of propylene and/or acrolein, is used as the high boiling impurities containing acrylic acid dimer, acrylic acid and maleic acid; and a distillation column equipped with a thin film vaporizer is used as the acrylic acid recovery column.

Appended FIG. 1 is a flow chart showing an embodiment of working the method of the present invention. High boiling impurities containing acrylic acid dimer, acrylic acid, maleic acid, etc., which are obtained from bottom part of a high boiling impurities separation column 1 are introduced into a distillation column 2 equipped with a thin film vaporizer 3, wherein acrylic acid is distilled and recovered. The maleic acid content of the distilled acrylic acid in that occasion is markedly reduced, which ranges 0 to 3% by weight, preferably 0 to 1% by weight. Thus recovered acrylic acid is normally recirculated to a preceding step, eg., a purification step, more specifically, into the high boiling impurities separation column 1, to provide product acrylic acid.

It is desirable to select the design and operation conditions of distillation column 2 so as to carry out the above separation of maleic acid with high efficiency. Specifically, as the distillation column 2, a tray tower with a theoretical number of tray(s) ranging from 1 to 5, preferably 1 to 3, having dual flow porous plate(s) is conveniently used. Moreover, it is desirable to carry out the distillation operation under a reduced pressure, preferably under pressure of 10 to 100 mmHg, and under such conditions that the bottom temperature of the distillation column 2 should be not higher than 120° C., preferably within a range of 60 to 120° C. When the bottom temperature of the column is too high, precipitate which is considered to be attributable to maleic acid is formed to render safe operation over prolonged period difficult.

The thin film vaporizer 3 is subject to no critical limitation, and any of those conventionally used as thin film vaporizers can be used.

Bottom liquid A collected in the thin film vaporizer 3 is introduced into a pyrolyzing tank 4 seated in the next, where acrylic acid dimer is thermally decomposed and converted into acrylic acid. Pyrolyzing tank 4 is subject to no critical limitation but any which is suitable for thermal decomposition of acrylic acid dimer in bottom liquid A into acrylic acid can be used.

The pyrolyzing temperature at the pyrolyzing tank 4 normally ranges 120 to 220° C., in particular, pyrolysis at 120 to 160° C. is convenient. Residence time (capacity of pyrolyzing tank/amount of bottom liquid A) cannot be generally defined as it varies depending on the pyrolyzing temperature, while normally a residence time of around 20 to 50 hours is required. When the pyrolysis is conducted at very high temperature and for a short time, undesirable decomposition, polymerization and the like are apt to take place.

Acrylic acid dimer is thermally decomposed into acrylic acid in the pyrolyzing tank 4. For the purpose of recovering acrylic acid from the decomposition product, at least a part of bottom liquid B of the pyrolyzing tank 4 is recirculated into the thin film vaporizer 3 through the route indicated with solid line in the figure, and/or into the distillation column 2 through the route indicated with broken line in the same FIGURE. The remainder is discarded as waste liquid.

For efficiently recovering acrylic acid in the bottom liquid B, the recirculated amount of the bottom liquid B into the thin film vaporizer and/or distillation column 2 is increased, which is normally 1 to 20 weight times, preferably 3 to 20 weight times, that of the high boiling impurities containing acrylic acid dimer, acrylic acid and maleic acid. While the bottom liquid B may be recirculated into the high boiling impurities separation column 1, such is liable to cause concentration of maleic acid at the bottom part of the high boiling impurities separation column 1 and precipitates in certain occasions. It is therefore preferred to recirculate the bottom liquid B into thin film vaporizer 3 and/or distillation column 2.

The acrylic acid recovered from the top of the distillation column 2 is normally recirculated into a preceding step, for example, purification step, more specifically into the high boiling impurities separation column 1, and recovered as the final product acrylic acid. The acrylic acid recovered from the top of the distillation column 2 contains only very little amount of maleic acid and therefore concentration of maleic acid in th purification step does not take place and purity of the product acrylic acid is not reduced. Furthermore, the greatest part of maleic acid is separated and removed as waste liquid, and hence occurrence of troubles due to formation of precipitate attributable thereto can be markedly reduced.

Hereinafter the present invention is explained in more detail, referring to a working Example.

EXAMPLE

Acrylic acid was recovered following the flow chart of FIG. 1. Particulars of the distillation column 2, thin film vaporizer 3 and pyrolizing tank 4 were as follows:

distillation column 2: plate number 15, dual flow porous plate distillation column thin film vaporizer 3: heat transfer area 7.5 m$^2$, horizontal type pyrolyzing tank 4: capacity 11 m$^3$.

The high boiling impurities containing acrylic acid dimer, acrylic acid and maleic acid, which were obtained through gas-phase catalytic oxidation step of propylene, trapping step, azeotropic separation step and purification step (high boiling impurities separation column 1), were introduced into the central plate of distillation column 2, at a flow rate of 0.7 t/hr.

In the distillation column 2, the thin film vaporizer 3 was regulated so as to make the temperature at the bottom of the column 85° C., and the column was operated under the conditions of an operation pressure at 25 mmHg and at a reflux ratio of 0.9. Acrylic acid was recovered from the column top at a rate of 0.5 t/hr. (Hereafter this acrylic acid is referred to as the recovered acrylic acid).

Bottom liquid A from the thin film vaporizer 3 was introduced into a pyrolyzing tank 4 and thermally decomposed therein under the conditions of at an inside temperature of the tank of 140° C. and residence time of 45 hours. A part of the resultant bottom liquid B was recirculated into the thin film vaporizer 3. The flow rate of the recirculated bottom liquid B was 2.8 t/hr, which was 4 weight times that of the high boiling impurities containing acrylic acid dimer, acrylic acid and maleic acid. The rest was discarded as waste liquid.

The compositions of the high boiling impurities, recovered acrylic acid and the waste liquid were as in Table 1.

TABLE 1

| | Acrylic acid | Acrylic acid dimer | Maleic acid | Other impurities |
|---|---|---|---|---|
| High boiling impurities | 53.2 | 31.5 | 5.2 | 10.1 |
| Recovered acrylic acid | 99.1 | 0.04 | 0.5 | 0.4 |
| Waste liquid | 5.4 | 28.7 | 4.8 | 61.1 |

Unit: weight %

The above operation was continued for 6 months. The operation was stable and free of such a problem as precipitation. The purification yield was 98%, and the decomposition ratio of acrylic acid dimer was 73.9%.

As is understood from the above Example, according to the present invention acrylic acid dimer can be efficiently decomposed, to increase recovery ratio of acrylic acid. According to the present invention, furthermore, the acrylic acid recovered from the top of acrylic acid recovery column (distillation column) contains only very little amount of maleic acid, and when it is recirculated into the purification step, it causes little accumulation of maleic acid in said step. Hence, the method is free from the fear of reduction in purity of the product acrylic acid resulting from mixing of maleic acid into the product.

Thus, according to the invention acrylic acid can be recovered from acrylic acid dimer with high efficiency and high purity acrylic acid can be produced. Moreover, because the invention can prevent formation of precipitate attributable to maleic acid, safe operation over prolonged periods is realized.

What is claimed is:

1. A method for recovering acrylic acid from high boiling impurities containing acrylic acid dimer, acrylic acid and maleic acid, wherein the high boiling impurities containing acrylic acid dimer, acrylic acid and maleic acid is a bottom liquid obtained from a high boiling impurities separation column used in the process comprising contacting an acrylic acid-containing gas resulting from gas-phase catalytic oxidation of propylene and/or acrolein with water to trap the acrylic acid in the form of an aqueous acrylic acid solution, distilling the aqueous solution in an azeotropic separation column in the presence of an azeotropic solvent, and purifying the resultant crude acrylic acid obtained from the bottom part of said azeotropic separation column in said high boiling impurities separation column, by a process which comprises (1) introducing said high boiling impurities containing acrylic acid dimer, acrylic acid and maleic acid, into an acrylic acid recovery column and recovering acrylic acid as it is distilled off from the top of the column, (2) introducing bottom liquid A from said acrylic acid recovery column into a pyrolyzing tank to decompose the acrylic acid dimer in the bottom liquid A, and then, (3) recirculating at least a part of bottom liquid B from said pyrolyzing tank into the acrylic acid recovery column.

2. A method according to claim 1 in which the acrylic acid recovery column is a distillation column equipped with a thin film vaporizer.

3. A method according to claim 1 in which the pyrolyzing temperature is 120 to 220° C.

4. A method according to claim 1, 2 or 3, in which the recirculated amount of the bottom liquid B from the pyrolyzing tank is 1 to 20 times that of the high boiling impurities containing acrylic acid dimer, acrylic acid and maleic acid.

5. A method for recovering acrylic acid from an acrylic acid recovery process comprising contacting an acrylic acid-containing gas obtained through gas-phase catalytic oxidation of propylene and/or acrolein with water to trap the acrylic acid in the form of its aqueous solution, distilling said aqueous acrylic acid solution in an azeotropic separation column in the presence of an azeotropic solvent, and purifying the crude acrylic acid obtained from the bottom part of said azeotropic separation column in a high boiling impurities separation column, which method comprises recovering acrylic acid from said high boiling impurities containing acrylic acid dimer, acrylic acid and maleic acid as obtained from the bottom part of the high boiling impurities separation column, and (1) introducing said high boiling impurities containing acrylic acid dimer, acrylic acid and maleic acid into an acrylic acid recovery column composed of a distillation column equipped with a thin film vaporizer, wherein conducting distillation under conditions of 10 to 100 mmHg and at the bottom temperature of the column of 60 to 120° C., distilling acrylic acid off from the column top and recovering the same;

(2) introducing bottom liquid A from said thin film vaporizer into a pyrolyzing tank, whereat decomposing acrylic acid dimer in said bottom liquid A at temperatures of 120 to 220° C.; and thereafter (3) recirculating at least a part of bottom liquid B of said pyrolyzing tank into said distillation column and/or thin film vaporizer, at a ratio of 1 to 20 times in volume to the high boiling impurities containing acrylic acid dimer, acrylic acid and maleic acid.

6. A method according to claim 2 in which the pyrolyzing temperature is 120 to 220° C.

7. A method for recovering acrylic acid which consists essentially of recovering acrylic acid from high boiling impurities containing acrylic acid dimer, acrylic acid and maleic acid obtained from the bottom part of a high boiling impurities separation column, and (1) introducing said high boiling impurities containing acrylic acid dimer, acrylic acid and maleic acid into an acrylic acid recovery column composed of a distillation column equipped with a thin film vaporizer, wherein conducting distillation under conditions of 10 to 100 mmHg and at the bottom temperature of the column of 60 to 120°C., distilling acrylic acid off from the column top and recovering the same;

(2) introducing bottom liquid A from said thin film vaporizer into a pyrolyzing tank, whereat decomposing acrylic acid dimer in said bottom liquid A at temperatures of 120 to 220° C.; and thereafter (3) recirculating at least a part of bottom liquid B of said pyrolyzing tank into said distillation column and/or thin vaporizer, at a ratio of 1 to 20 times in volume to the high boiling impurities containing acrylic acid dimer, acrylic acid and maleic acid.

8. A method for recovering acrylic acid from high boiling impurities containing acrylic acid diner, acrylic acid and maleic acid, wherein the high boiling impurities containing acrylic acid dimer, acrylic acid and maleic acid is a bottom liquid obtained from a high boiling impurities separation column used in the process comprising contacting an acrylic acid-containing gas resulting from gas-phase catalytic oxidation of propylene and/or acrolein with water to trap the acrylic acid in the form of an aqueous acrylic acid solution, distilling the aqueous solution in an azeotropic separation column in the presence of an azeotropic solvent, and purifying the resultant crude acrylic acid obtained from the bottom part of said azeotropic separation column in said high boiling impurities separation column, by a process which comprises (1) introducing said high boiling impurities containing acrylic acid dimer, acrylic acid and maleic acid, into an acrylic acid recovery column operated under reduced pressure and at temperatures at the bottom part of the column ranging from 60 to 120° C. and recovering acrylic acid as it is distilled off from the top of the column, (2) introducing bottom liquid A from said acrylic acid recovery column into a pyrolyzing tank to decompose the acrylic acid dimer in the bottom liquid A, and then, (3) recirculating at least a part of bottom liquid B from said pyrolyzing tank into the acrylic acid recovery column.

9. A method according to claim 8 in which the acrylic acid recovery column is a distillation column equipped with a thin film vaporizer.

10. A method according to claim 8 in which the pyrolyzing temperature is 120 to 220° C.

* * * * *